(12) United States Patent
Jain

(10) Patent No.: US 12,089,658 B2
(45) Date of Patent: Sep. 17, 2024

(54) VAPOR DIAGNOSTIC SYSTEM

(71) Applicant: NICOVENTURES TRADING LIMITED, London (GB)

(72) Inventor: Siddhartha Jain, London (GB)

(73) Assignee: NICOVENTURES TRADING LIMITED, London (GB)

( * ) Notice: Subject to any disclaimer, the term of this patent is extended or adjusted under 35 U.S.C. 154(b) by 566 days.

(21) Appl. No.: 17/309,283

(22) PCT Filed: Oct. 3, 2019

(86) PCT No.: PCT/GB2019/052786
§ 371 (c)(1),
(2) Date: May 14, 2021

(87) PCT Pub. No.: WO2020/099821
PCT Pub. Date: May 22, 2020

(65) Prior Publication Data
US 2021/0401063 A1 Dec. 30, 2021

(30) Foreign Application Priority Data
Nov. 16, 2018 (GB) .................................. 1818720

(51) Int. Cl.
*A24F 40/60* (2020.01)
*A24F 40/51* (2020.01)
(Continued)

(52) U.S. Cl.
CPC .............. *A24F 40/60* (2020.01); *A24F 40/51* (2020.01); *A24F 40/53* (2020.01); *G01N 33/4972* (2013.01)

(58) Field of Classification Search
CPC .......... A24F 40/60; A24F 40/51; A24F 40/53; A24F 40/00; A24F 40/485; A24F 40/65;
(Continued)

(56) References Cited

U.S. PATENT DOCUMENTS 11,829,994 B1 * 11/2023 Kurani .................. G06Q 50/01
11,975,769 B2 * 5/2024 Lacroix ............... B62D 35/001
(Continued)

FOREIGN PATENT DOCUMENTS

CN    203986134 U    12/2014
CN    204599337 U    9/2015
(Continued)

OTHER PUBLICATIONS

International Search Report and Written Opinion for PCT/GB2019/052786 date mailed Feb. 17, 2020, 14 pages.
(Continued)

*Primary Examiner* — Truc T Nguyen
(74) *Attorney, Agent, or Firm* — Burr & Forman LLP

(57) ABSTRACT

A user monitoring system includes an e-cigarette including a power source, and an electronic breath alcohol testing device for detecting alcohol detachable from the e-cigarette, in which when attached, the electronic breath alcohol testing device is operable to share at least part of an airflow path of the e-cigarette, and when attached, the electronic breath alcohol testing device is operable to share the power source of the e-cigarette.

20 Claims, 9 Drawing Sheets

(51) Int. Cl.
*A24F 40/53* (2020.01)
*G01N 33/497* (2006.01)

(58) Field of Classification Search
CPC ..... A24F 40/46; G01N 33/4972; H04W 4/80; H04W 88/02
See application file for complete search history.

(56) References Cited

U.S. PATENT DOCUMENTS

| | | |
|---|---|---|
| 2013/0220315 A1 | 8/2013 | Conley et al. |
| 2017/0027232 A1 | 2/2017 | Scheck et al. |
| 2017/0086504 A1 | 3/2017 | Cameron |
| 2017/0092106 A1 | 3/2017 | Cameron |
| 2017/0093960 A1 | 3/2017 | Cameron |
| 2017/0093981 A1 | 3/2017 | Cameron |
| 2017/0115273 A1 | 4/2017 | Wu |
| 2017/0135412 A1 | 5/2017 | Cameron |
| 2018/0007970 A1* | 1/2018 | Sur .................. A24F 40/40 |
| 2018/0228218 A1* | 8/2018 | Chu .................. A24F 40/00 |
| 2018/0263283 A1 | 9/2018 | Popplewell et al. |
| 2019/0158938 A1* | 5/2019 | Bowen ............... H04W 4/20 |
| 2020/0268058 A1 | 8/2020 | Chiang et al. |
| 2023/0372148 A1* | 11/2023 | O'Leary ............. A61F 7/0085 |

FOREIGN PATENT DOCUMENTS

| | | |
|---|---|---|
| JP | 2009008499 A | 1/2009 |
| KR | 20010083306 A | 9/2001 |
| KR | 20120094400 A | 8/2012 |
| KR | 20180016995 | 2/2018 |
| KR | 20210016769 A | 2/2021 |
| WO | WO-2014036088 A1 | 3/2014 |
| WO | WO-2018007937 A2 | 1/2018 |

OTHER PUBLICATIONS

Search Report under Section 17(5) for Great Britain Application No. GB1818720.3, mailed May 9, 2019, 4 pages.
International Preliminary Report on Patentability for Application No. PCT/GB2019/052786, mailed on May 27, 2021, 9 pages.
Office Action for Japanese Application No. 2021-525193, mailed on Jun. 28, 2022, 34 pages.
Search Report for Japanese Application No. 2021-525193, mailed Jun. 30, 2022, 25 pages.
Office Action from corresponding Korean Application No. 10-2024-7012057 mailed Apr. 18, 2024, all pages cited in its entirety.

* cited by examiner

VAPOR DIAGNOSTIC SYSTEM

PRIORITY CLAIM

The present application is a National Phase entry of PCT Application No. PCT/GB2019/052786, filed Oct. 3, 2019, which claims priority from GB Patent Application No. 1818720.3, filed Nov. 16, 2018, each of which is hereby fully incorporated herein by reference.

TECHNICAL FIELD

The present disclosure relates to a vapor diagnostic system.

BACKGROUND

It is common for a person to drink and vape (i.e. use an e-cigarette) in social situations. However, alcohol consumption is also associated with various regulations in relation to driving and other activities. Consequently, it would be desirable for that person to be able to assess their blood alcohol levels in a convenient manner in these circumstances.

SUMMARY

In a first aspect, a user monitoring system is provided in accordance with embodiments of the disclosure.

In another aspect, an e-cigarette is provided in accordance with embodiments of the disclosure.

In another aspect, an electronic breath alcohol testing device is provided in accordance with embodiments of the disclosure.

In another aspect, the mobile terminal is provided in accordance with embodiments of the disclosure.

Further respective aspects and features of the disclosure are defined in the appended claims.

BRIEF DESCRIPTION OF THE DRAWINGS

Embodiments of the present disclosure will now be described by way of example with reference to the accompanying drawings, in which.

DETAILED DESCRIPTION

Figure 1:
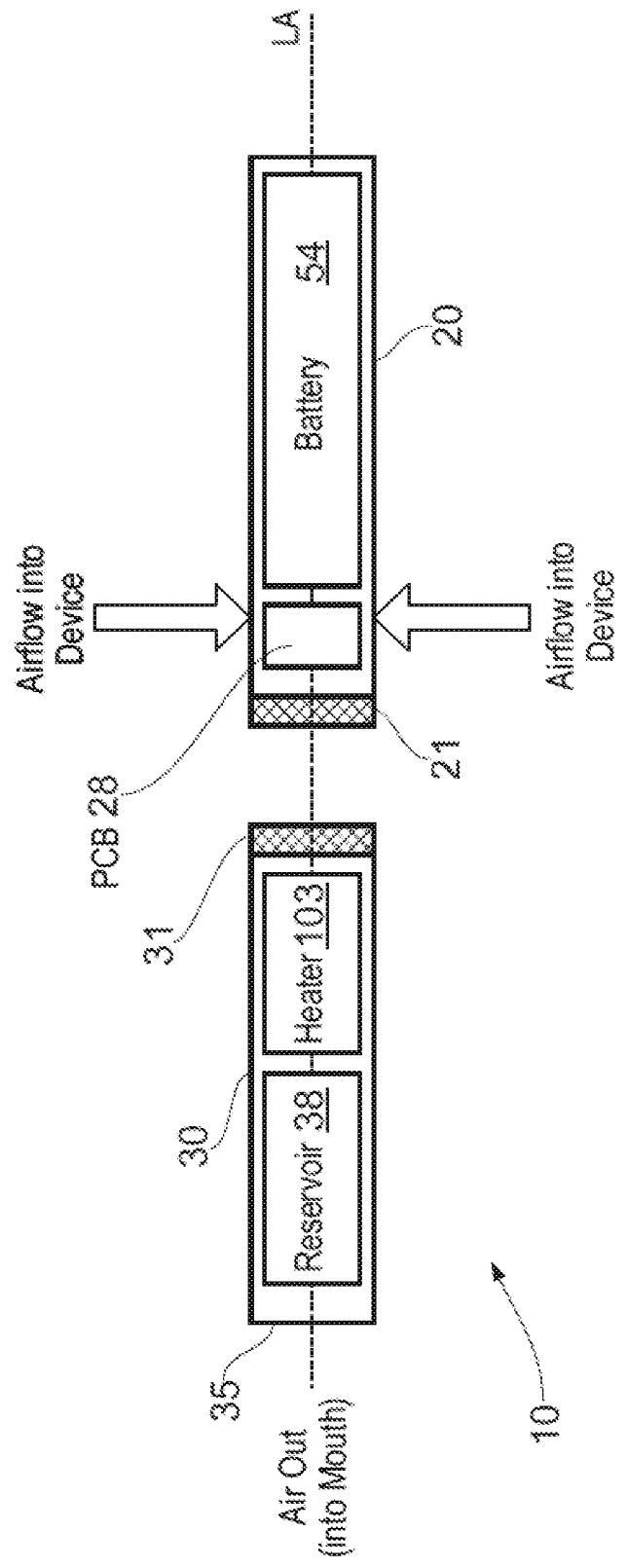
FIG. 1 is a schematic diagram of an e-cigarette in accordance with embodiments of the present disclosure.

A vapor diagnostic system is disclosed. In the following description, a number of specific details are presented in order to provide a thorough understanding of the embodiments of the present disclosure. It will be apparent, however, to a person skilled in the art that these specific details need not be employed to practice the present disclosure. Conversely, specific details known to the person skilled in the art are omitted for the purposes of clarity where appropriate.

In embodiments of the present disclosure, a user monitoring system (being a vapor diagnostic system or breath analysis system) comprises a fully functioning e-cigarette comprising its own power supply, and a breath alcohol testing device for detecting alcohol, in which the electronic breath alcohol testing device shares at least part of an airflow path with the e-cigarette, and the electronic breath alcohol testing device takes power from the e-cigarette.

In embodiments of the present disclosure, the breath alcohol testing device is attachable/detachable from the e-cigarette, thereby avoiding the need to carry (and potentially power) the breath alcohol testing device component when it is not needed, for example during the working day.

In embodiments of the present disclosure, attaching the breath alcohol testing device causes it to access or divert the flow path of the e-cigarette; alternatively or in addition, one of the breath alcohol testing device and the e-cigarette are manipulable to provide access to the airflow path of the e-cigarette or divert it to the breath alcohol testing device.

In embodiments of the present disclosure, the e-cigarette comprises a valve or similar flow biasing means to prevent or reduce blowback into the e-cigarette when operating the breath alcohol testing device.

In embodiments of the present disclosure, the breath alcohol testing device is adapted to distinguish between signals attributable to alcohol and signals attributable to a solvent of an e-liquid used for generating vapor by the e-cigarette.

It is known, for example from CN203986134U, to provide a power supply and alcohol testing device that can be attached to an e-cigarette atomizer. Notably however in this case the alcohol testing device is integral to the unit comprising the power supply and hence the e-cigarette cannot be operated without also carrying the alcohol testing device. Furthermore it is also clear that the alcohol testing device, which is positioned next to a USB port, is intended to be blown upon directly by the user and does not share an airflow path with the e-cigarette atomizer itself.

By way of background explanation, electronic vapor provision systems, such as e-cigarettes and other aerosol delivery systems, generally contain a reservoir of liquid which is to be vaporized, typically nicotine (this is sometimes referred to as an "e-liquid"). When a user inhales on the device, an electrical (e.g. resistive) heater is activated to vaporize a small amount of liquid, in effect producing an aerosol which is therefore inhaled by the user. The liquid may comprise nicotine in a solvent, such as ethanol or water, together with glycerine or propylene glycol to aid aerosol formation, and may also include one or more additional flavors. The skilled person will be aware of many different liquid formulations that may be used in e-cigarettes and other such devices.

The practice of inhaling vaporized liquid in this manner is commonly known as 'vaping'.

An e-cigarette may have an interface to support external data communications. This interface may be used, for example, to load control parameters and/or updated software onto the e-cigarette from an external source. Alternatively or additionally, the interface may be utilized to download data from the e-cigarette to an external system. The downloaded data may, for example, represent usage parameters of the e-cigarette, fault conditions, etc. As the skilled person will be aware, many other forms of data can be exchanged between an e-cigarette and one or more external systems (which may be another e-cigarette).

In some cases, the interface for an e-cigarette to perform communication with an external system is based on a wired connection, such as a USB link using a micro, mini, or ordinary USB connection into the e-cigarette. The interface for an e-cigarette to perform communication with an external system may also be based on a wireless connection. Such a wireless connection has certain advantages over a wired connection. For example, a user does not need any additional cabling to form such a connection. In addition, the user has more flexibility in terms of movement, setting up a connection, and the range of pairing devices.

Throughout the present description the term "e-cigarette" is used; however, this term may be used interchangeably with electronic vapor provision system, aerosol delivery device, and other similar terminology.

FIG. 1 is a schematic (exploded) diagram of an e-cigarette 10 in accordance with some embodiments of the disclosure (not to scale). The e-cigarette comprises a body or control unit 20 and a cartomizer 30. The cartomizer 30 includes a reservoir 38 of liquid, typically including nicotine, a heater 36, and a mouthpiece 35. The e-cigarette 10 has a longitudinal or cylindrical axis which extends along the center-line of the e-cigarette from the mouthpiece 35 at one end of the cartomizer 30 to the opposing end of the control unit 20 (usually referred to as the tip end). This longitudinal axis is indicated in FIG. 1 by the dashed line denoted LA.

The liquid reservoir 38 in the cartomizer may hold the (e-)liquid directly in liquid form, or may utilize some absorbing structure, such as a foam matrix or cotton material, etc, as a retainer for the liquid. The liquid is then fed from the reservoir 38 to be delivered to a vaporizer comprising the heater 36. For example, liquid may flow via capillary action from the reservoir 38 to the heater 36 via a wick (not shown in FIG. 1).

In other devices, the liquid may be provided in the form of plant material or some other (ostensibly solid) plant derivative material. In this case the liquid can be considered as representing volatiles in the material which vaporize when the material is heated. Note that devices containing this type of material generally do not require a wick to transport the liquid to the heater, but rather provide a suitable arrangement of the heater in relation to the material to provide suitable heating.

It will also be appreciated that forms of payload delivery other than a liquid may be equally considered, such as heating a solid material (such as processed tobacco leaf) or a gel. In such cases, the volatiles that vaporize provide the active ingredient of the vapor/aerosol to be inhaled. It will be understood that references herein to 'liquid', 'e-liquid' and the like equally encompass other modes of payload delivery, and similarly references to 'reservoir' or similar equally encompass other means of storage, such as a container for solid materials.

The control unit 20 includes a re-chargeable cell or battery 54 to provide power to the e-cigarette 10 (referred to hereinafter as a battery) and a printed circuit board (PCB) 28 and/or other electronics for generally controlling the e-cigarette.

The control unit 20 and the cartomizer 30 are detachable from one another, as shown in FIG. 1, but are joined together when the device 10 is in use, for example, by a screw or bayonet fitting. The connectors on the cartomizer 30 and the control unit 20 are indicated schematically in FIG. 1 as 31B and 21A respectively. This connection between the control unit and cartomizer provides for mechanical and electrical connectivity between the two.

When the control unit is detached from the cartomizer, the electrical connection 21A on the control unit that is used to connect to the cartomizer may also serve as a socket for connecting a charging device (not shown). The other end of this charging device can be plugged into a USB socket to re-charge the battery 54 in the control unit of the e-cigarette. In other implementations, the e-cigarette may be provided (for example) with a cable for direct connection between the electrical connection 21A and a USB socket.

The control unit is provided with one or more holes for air inlet adjacent to PCB 28. These holes connect to an air passage through the control unit to an air passage provided through the connector 21A. This then links to an air path through the cartomizer 30 to the mouthpiece 35. Note that the heater 36 and the liquid reservoir 38 are configured to provide an air channel between the connector 31B and the mouthpiece 35. This air channel may flow through the center of the cartomizer 30, with the liquid reservoir 38 confined to an annular region around this central path. Alternatively (or additionally) the airflow channel may lie between the liquid reservoir 38 and an outer housing of the cartomizer 30.

When a user inhales through the mouthpiece 35, air is drawn into the control unit 20 through the one or more air inlet holes. This airflow (or the associated change in pressure) is detected by a sensor, e.g. a pressure sensor, which in turn activates the heater 36 to vaporize the nicotine liquid fed from the reservoir 38. The airflow passes from the control unit into the vaporizer, where the airflow combines with the nicotine vapor. This combination of airflow and nicotine vapor (in effect, an aerosol) then passes through the cartomizer 30 and out of the mouthpiece 35 to be inhaled by a user. The cartomizer 30 may be detached from the control unit and disposed of when the supply of nicotine liquid is exhausted (and then replaced with another cartomizer).

It will be appreciated that the e-cigarette 10 shown in FIG. 1 is presented by way of example only, and many other implementations may be adopted. For example, in some implementations, the cartomizer 30 is split into a cartridge containing the liquid reservoir 38 and a separate vaporizer portion containing the heater 36. In this configuration, the cartridge may be disposed of after the liquid in reservoir 38 has been exhausted, but the separate vaporizer portion containing the heater 36 is retained. Alternatively, an e-cigarette may be provided with a cartomizer 30 as shown in FIG.

1, or else constructed as a one-piece (unitary) device, but the liquid reservoir 38 is in the form of a (user-) replaceable cartridge. Further possible variations are that the heater 36 may be located at the opposite end of the cartomizer 30 from that shown in FIG. 1, i.e. between the liquid reservoir 38 and the mouthpiece 35, or else the heater 36 is located along a central axis LA of the cartomizer, and the liquid reservoir is in the form of an annular structure which is radially outside the heater 35.

The skilled person will also be aware of a number of possible variations for the control unit 20. For example, airflow may enter the control unit at the tip end, i.e. the opposite end to connector 21A, in addition to or instead of the airflow adjacent to PCB 28. In this case the airflow would typically be drawn towards the cartomizer along a passage between the battery 54 and the outer wall of the control unit. Similarly, the control unit may comprise a PCB located on or near the tip end, e.g. between the battery and the tip end. Such a PCB may be provided in addition to or instead of PCB 28.

Furthermore, an e-cigarette may support charging at the tip end, or via a socket elsewhere on the device, in addition to or in place of charging at the connection point between the cartomizer and the control unit. (It will be appreciated that some e-cigarettes are provided as essentially integrated units, in which case a user is unable to disconnect the cartomizer from the control unit). Other e-cigarettes may also support wireless (induction) charging, in addition to (or instead of) wired charging.

The above discussion of potential variations to the e-cigarette shown in FIG. 1 is by way of example. The skilled person will aware of further potential variations (and combination of variations) for the e-cigarette 10.

Figure 2:
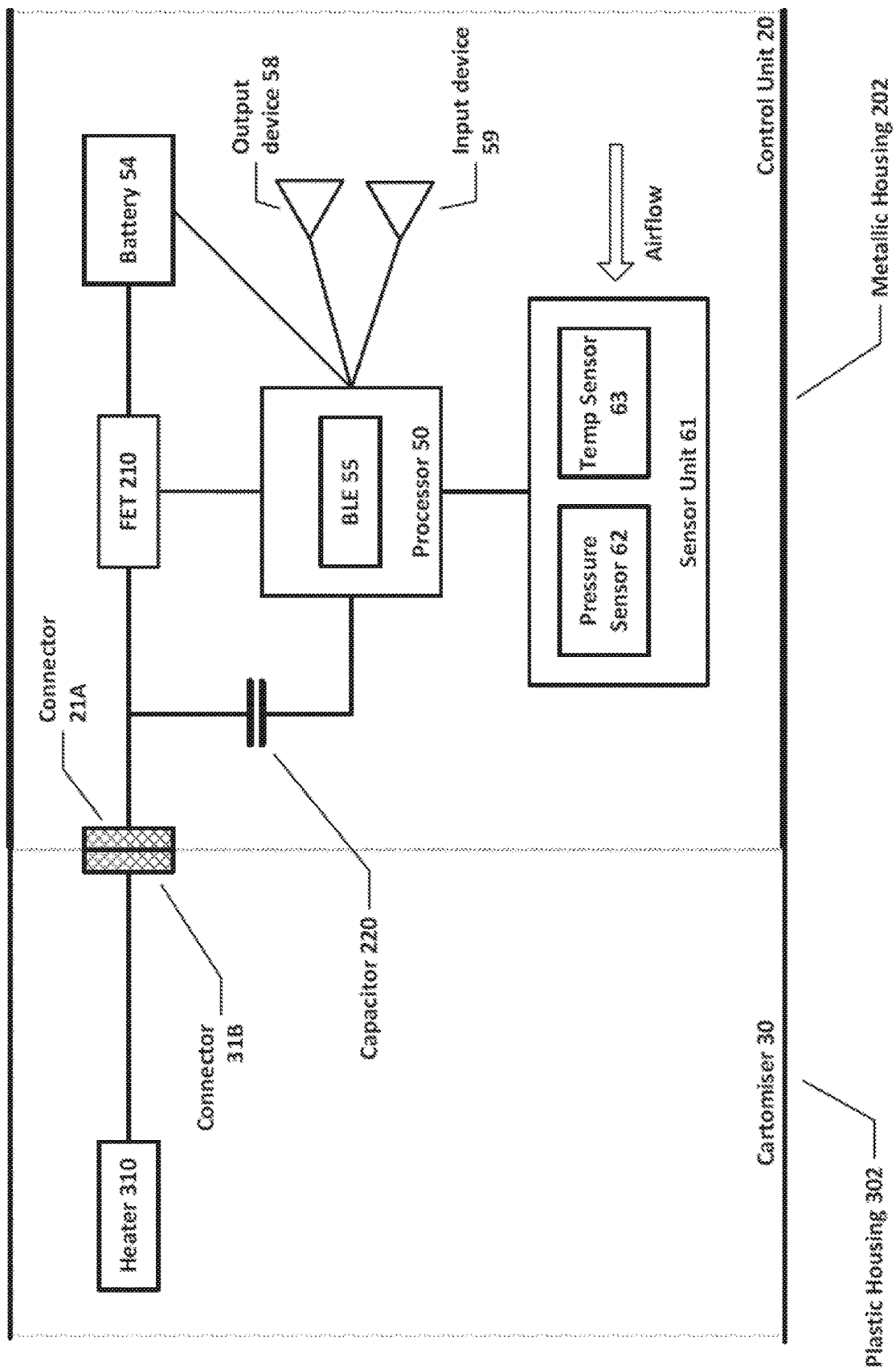
FIG. 2 is a schematic diagram of a control unit of an e-cigarette in accordance with embodiments of the present disclosure.

FIG. 2 is a schematic diagram of the main functional components of the e-cigarette 10 of FIG. 1 in accordance with some embodiments of the disclosure. N.B. FIG. 2 is primarily concerned with electrical connectivity and functionality—it is not intended to indicate the physical sizing of the different components, nor details of their physical placement within the control unit 20 or cartomizer 30. In addition, it will be appreciated that at least some of the components shown in FIG. 2 located within the control unit 20 may be mounted on the circuit board 28. Alternatively, one or more of such components may instead be accommodated in the control unit to operate in conjunction with the circuit board 28, but not physically mounted on the circuit board itself. For example, these components may be located on one or more additional circuit boards, or they may be separately located (such as battery 54).

As shown in FIG. 2, the cartomizer contains heater 310 which receives power through connector 31B. The control unit 20 includes an electrical socket or connector 21A for connecting to the corresponding connector 31B of the cartomizer 30 (or potentially to a USB charging device). This then provides electrical connectivity between the control unit 20 and the cartomizer 30.

The control unit 20 further includes a sensor unit 61, which is located in or adjacent to the air path through the control unit 20 from the air inlet(s) to the air outlet (to the cartomizer 30 through the connector 21A). The sensor unit contains a pressure sensor 62 and temperature sensor 63 (also in or adjacent to this air path). The control unit further includes a capacitor 220, a processor 50, a field effect transistor (FET) switch 210, a battery 54, and input and output devices 59, 58.

The operations of the processor 50 and other electronic components, such as the pressure sensor 62, are generally controlled at least in part by software programs running on the processor (or other components). Such software programs may be stored in non-volatile memory, such as ROM, which can be integrated into the processor 50 itself, or provided as a separate component. The processor 50 may access the ROM to load and execute individual software programs as and when required. The processor 50 also contains appropriate communications facilities, e.g. pins or pads (plus corresponding control software), for communicating as appropriate with other devices in the control unit 20, such as the pressure sensor 62.

The output device(s) 58 may provide visible, audio and/or haptic output. For example, the output device(s) may include a speaker 58, a vibrator, and/or one or more lights. The lights are typically provided in the form of one or more light emitting diodes (LEDs), which may be the same or different colors (or multi-colored). In the case of multi-colored LEDs, different colors are obtained by switching different colored, e.g. red, green or blue, LEDs on, optionally at different relative brightnesses to give corresponding relative variations in color. Where red, green and blue LEDs are provided together, a full range of colors is possible, whilst if only two out of the three red, green and blue LEDs are provided, only a respective sub-range of colors can be obtained.

The output from the output device may be used to signal to the user various conditions or states within the e-cigarette, such as a low battery warning. Different output signals may be used for signaling different states or conditions. For example, if the output device 58 is an audio speaker, different states or conditions may be represented by tones or beeps of different pitch and/or duration, and/or by providing multiple such beeps or tones. Alternatively, if the output device 58 includes one or more lights, different states or conditions may be represented by using different colors, pulses of light or continuous illumination, different pulse durations, and so on. For example, one indicator light might be utilized to show a low battery warning, while another indicator light might be used to indicate that the liquid reservoir 38 is nearly depleted. It will be appreciated that a given e-cigarette may include output devices to support multiple different output modes (audio, visual) etc.

The input device(s) 59 may be provided in various forms. For example, an input device (or devices) may be implemented as buttons on the outside of the e-cigarette—e.g. as mechanical, electrical or capacitive (touch) sensors. Some devices may support blowing into the e-cigarette as an input mechanism (such blowing may be detected by pressure sensor 62, which would then be also acting as a form of input device 59), and/or connecting/disconnecting the cartomizer 30 and control unit 20 as another form of input mechanism. Again, it will be appreciated that a given e-cigarette may include input devices 59 to support multiple different input modes.

As noted above, the e-cigarette 10 provides an air path from the air inlet through the e-cigarette, past the pressure sensor 62 and the heater 310 in the cartomizer 30 to the mouthpiece 35. Thus when a user inhales on the mouthpiece of the e-cigarette, the processor 50 detects such inhalation based on information from the pressure sensor 62. In response to such a detection, the CPU supplies power from the battery 54 to the heater, which thereby heats and vaporizes the nicotine from the liquid reservoir 38 for inhalation by the user.

In the particular implementation shown in FIG. 2, a FET 210 is connected between the battery 54 and the connector 21A. This FET 210 acts as a switch. The processor 50 is connected to the gate of the FET to operate the switch, thereby allowing the processor to switch on and off the flow of power from the battery 54 to heater 310 according to the status of the detected airflow. It will be appreciated that the heater current can be relatively large, for example, in the range 1-5 amps, and hence the FET 210 should be implemented to support such current control (likewise for any other form of switch that might be used in place of FET 210).

In order to provide more fine-grained control of the amount of power flowing from the battery 54 to the heater 310, a pulse-width modulation (PWM) scheme may be adopted. A PWM scheme may be based on a repetition period of say 1 ms. Within each such period, the switch 210 is turned on for a proportion of the period, and turned off for the remaining proportion of the period. This is parameterized by a duty cycle, whereby a duty cycle of 0 indicates that the switch is off for all of each period (i.e. in effect, permanently off), a duty cycle of 0.33 indicates that the switch is on for a third of each period, a duty cycle of 0.66 indicates that the switch is on for two-thirds of each period, and a duty cycle of 1 indicates that the FET is on for all of each period (i.e. in effect, permanently on). It will be appreciated that these are only given as example settings for the duty cycle, and intermediate values can be used as appropriate.

The use of PWM provides an effective power to the heater which is given by the nominal available power (based on the battery output voltage and the heater resistance) multiplied by the duty cycle. The processor 50 may, for example, utilize a duty cycle of 1 (i.e. full power) at the start of an inhalation to initially raise the heater 310 to its desired operating temperature as quickly as possible. Once this desired operating temperature has been achieved, the processor 50 may then reduce the duty cycle to some suitable value in order to supply the heater 310 with the desired operating power As shown in FIG. 2, the processor 50 includes a communications interface 55 for wireless communications, in particular, support for Bluetooth® Low Energy (BLE) communications.

Optionally the heater 310 may be utilized as an antenna for use by the communications interface 55 for transmitting and receiving the wireless communications. One motivation for this is that the control unit 20 may have a metal housing 202, whereas the cartomizer portion 30 may have a plastic housing 302 (reflecting the fact that the cartomizer 30 is disposable, whereas the control unit 20 is retained and therefore may benefit from being more durable). The metal housing acts as a screen or barrier which can affect the operation of an antenna located within the control unit 20 itself. However, utilizing the heater 310 as the antenna for the wireless communications can help to avoid this metal screening because of the plastic housing of the cartomizer, but without adding additional components or complexity (or cost) to the cartomizer. Alternatively a separate antenna may be provided (not shown), or a portion of the metal housing may be used.

If the heater is used as an antenna then as shown in FIG. 2, the processor 50, more particularly the communications interface 55, may be coupled to the power line from the battery 54 to the heater 310 (via connector 31B) by a capacitor 220. This capacitive coupling occurs downstream of the switch 210, since the wireless communications may operate when the heater is not powered for heating (as discussed in more detail below). It will be appreciated that capacitor 220 helps prevent the power supply from the battery 54 to the heater 310 being diverted back to the processor 50.

Note that the capacitive coupling may be implemented using a more complex LC (inductor-capacitor) network, which can also provide impedance matching with the output of the communications interface 55. (As known to the person skilled in the art, this impedance matching can help support proper transfer of signals between the communications interface 55 and the heater 310 acting as the antenna, rather than having such signals reflected back along the connection).

In some implementations, the processor 50 and communications interface are implemented using a Dialog DA14580 chip from Dialog Semiconductor PLC, based in Reading, United Kingdom. Further information (and a data sheet) for this chip is available www.dialog-semiconductor-.com.

Figure 3:
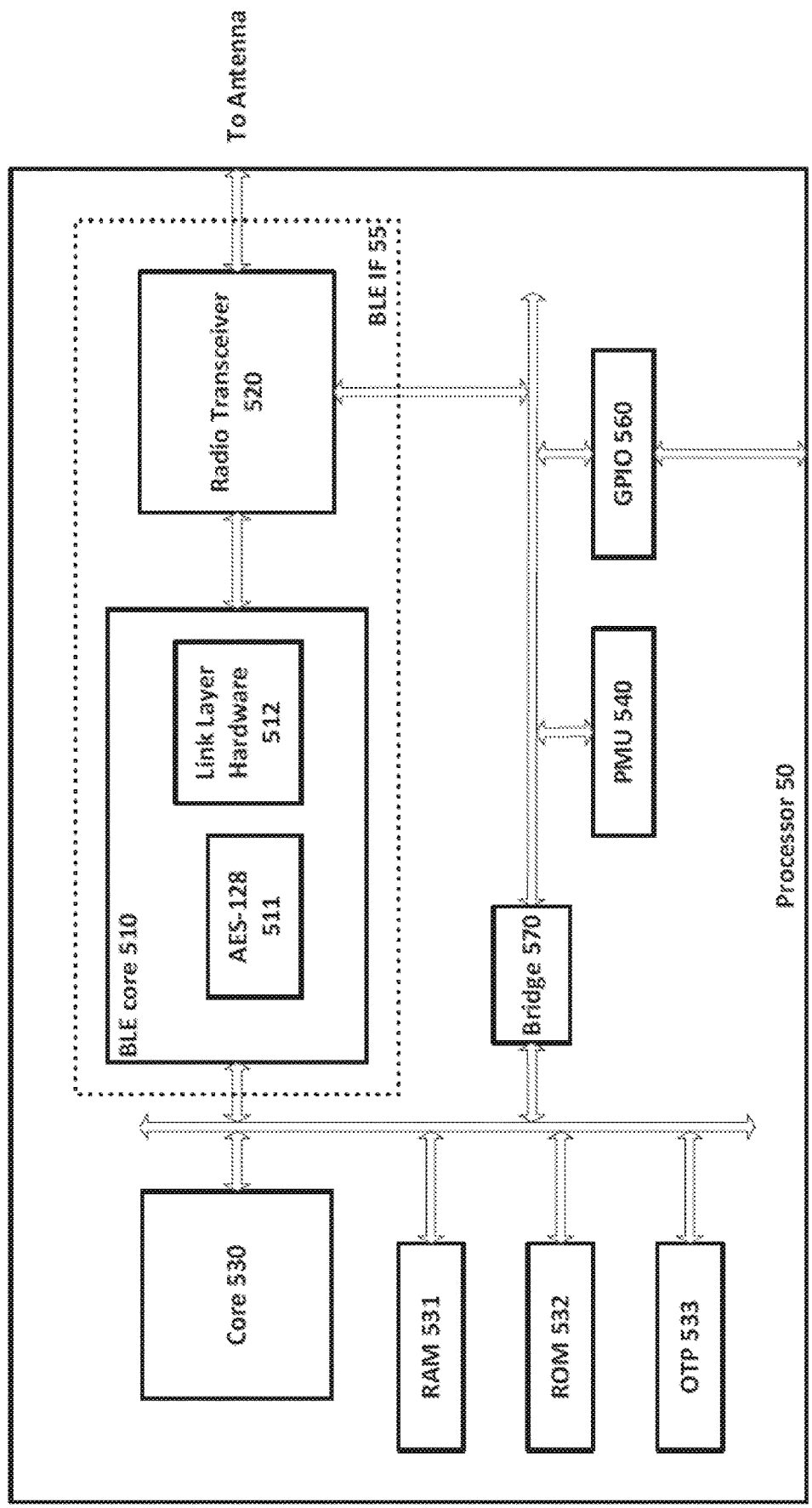
FIG. 3 is a schematic diagram of a processor of an e-cigarette in accordance with embodiments of the present disclosure.

FIG. 3 presents a high-level and simplified overview of this chip 50, including the communications interface 55 for supporting Bluetooth® Low Energy. This interface includes in particular a radio transceiver 520 for performing signal modulation and demodulation, etc., link layer hardware 512, and an advanced encryption facility (128 bits) 511. The output from the radio transceiver 520 is connected to the antenna (for example, to the heater 310 acting as the antenna via capacitive coupling 220 and connectors 21A and 31B).

The remainder of processor 50 includes a general processing core 530, RAM 531, ROM 532, a one-time programming (OTP) unit 533, a general purpose I/O system 560 (for communicating with other components on the PCB 28), a power management unit 540 and a bridge 570 for connecting two buses. Software instructions stored in the ROM 532 and/or OTP unit 533 may be loaded into RAM 531 (and/or into memory provided as part of core 530) for execution by one or more processing units within core 530. These software instructions cause the processor 50 to implement various functionality described herein, such as interfacing with the sensor unit 61 and controlling the heater accordingly. Note that although the device shown in FIG. 3 acts as both a communications interface 55 and also as a general controller for the electronic vapor provision system 10, in other embodiments these two functions may be split between two or more different devices (chips)—e.g. one chip may serve as the communications interface 55, and another chip as the general controller for the electronic vapor provision system 10.

In some implementations, the processor 50 may be configured to prevent wireless communications when the heater is being used for vaporizing liquid from reservoir 38. For example, wireless communications may be suspended, terminated or prevented from starting when switch 210 is switched on. Conversely, if wireless communications are ongoing, then activation of the heater may be prevented—e.g. by disregarding a detection of airflow from the sensor unit 61, and/or by not operating switch 210 to turn on power to the heater 310 while the wireless communications are progressing.

One reason for preventing the simultaneous operation of heater 310 for both heating and wireless communications in some implementations is to help avoid potential interference from the PWM control of the heater. This PWM control has its own frequency (based on the repetition frequency of the pulses), albeit typically much lower than the frequency used for the wireless communications, and the two could potentially interfere with one another. In some situations, such interference may not, in practice, cause any problems, and simultaneous operation of heater 310 for both heating and wireless communications may be allowed (if so desired). This may be facilitated, for example, by techniques such as the appropriate selection of signal strengths and/or PWM frequency, the provision of suitable filtering, etc.

Figure 4:
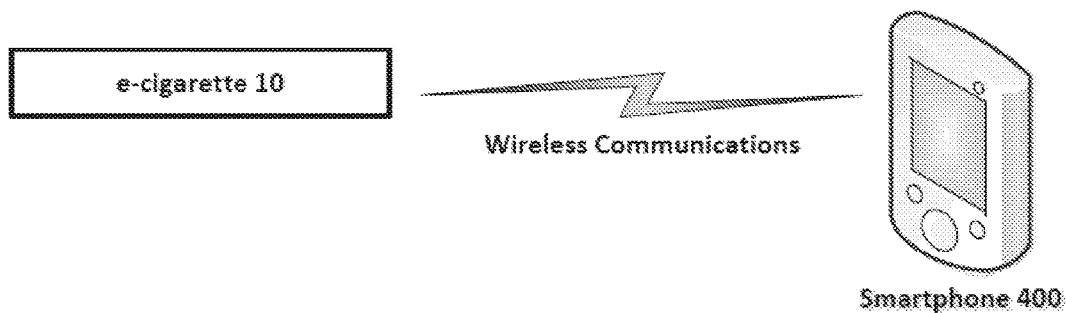
FIG. 4 is a schematic diagram of an e-cigarette in communication with a mobile terminal in accordance with embodiments of the present disclosure.

FIG. 4 is a schematic diagram showing Bluetooth® Low Energy communications between an e-cigarette 10 and an application (app) running on a smartphone 400 or other suitable mobile communication device (tablet, laptop, smartwatch, etc.). Such communications can be used for a wide range of purposes, for example, to upgrade firmware on the e-cigarette 10, to retrieve usage and/or diagnostic data from the e-cigarette 10, to reset or unlock the e-cigarette 10, to control settings on the e-cigarette, etc.

In general terms, when the e-cigarette 10 is switched on, such as by using input device 59, or possibly by joining the cartomizer 30 to the control unit 20, it starts to advertise for Bluetooth® Low Energy communication. If this outgoing communication is received by smartphone 400, then the smartphone 400 requests a connection to the e-cigarette 10. The e-cigarette may notify this request to a user via output device 58, and wait for the user to accept or reject the request via input device 59. Assuming the request is accepted, the e-cigarette 10 is able to communicate further with the smartphone 400. Note that the e-cigarette may remember the identity of smartphone 400 and be able to accept future connection requests automatically from that smartphone. Once the connection has been established, the smartphone 400 and the e-cigarette 10 operate in a client-server mode, with the smartphone operating as a client that initiates and sends requests to the e-cigarette which therefore operates as a server (and responds to the requests as appropriate).

A Bluetooth® Low Energy link (also known as Bluetooth Smart®) implements the IEEE 802.15.1 standard, and operates at a frequency of 2.4-2.5 GHz, corresponding to a wavelength of about 12 cm, with data rates of up to 1 Mbit/s. The set-up time for a connection is less than 6 ms, and the average power consumption can be very low—of the order 1 mW or less. A Bluetooth Low Energy link may extend up to some 50 m. However, for the situation shown in FIG. 4, the e-cigarette 10 and the smartphone 400 will typically belong to the same person, and will therefore be in much closer proximity to one another—e.g. 1 m. Further information about Bluetooth Low Energy can be found at www.bluetooth.com.

It will be appreciated that e-cigarette 10 may support other communications protocols for communication with smartphone 400 (or any other appropriate device). Such other communications protocols may be instead of, or in addition to, Bluetooth Low Energy. Examples of such other communications protocols include Bluetooth® (not the low energy variant), see for example, www.bluetooth.com, near field communications (NFC), as per ISO 13157, and WiFi®. NFC communications operate at much lower wavelengths than Bluetooth (13.56 MHz) and generally have a much shorter range—say <0.2 m. However, this short range is still compatible with most usage scenarios such as shown in FIG. 4. Meanwhile, low-power WiFi® communications, such as IEEE802.11ah, IEEE802.11v, or similar, may be employed between the e-cigarette 10 and a remote device. In each case, a suitable communications chipset may be included on PCB 28, either as part of the processor 50 or as a separate component. The skilled person will be aware of other wireless communication protocols that may be employed in e-cigarette 10.

Figure 5:
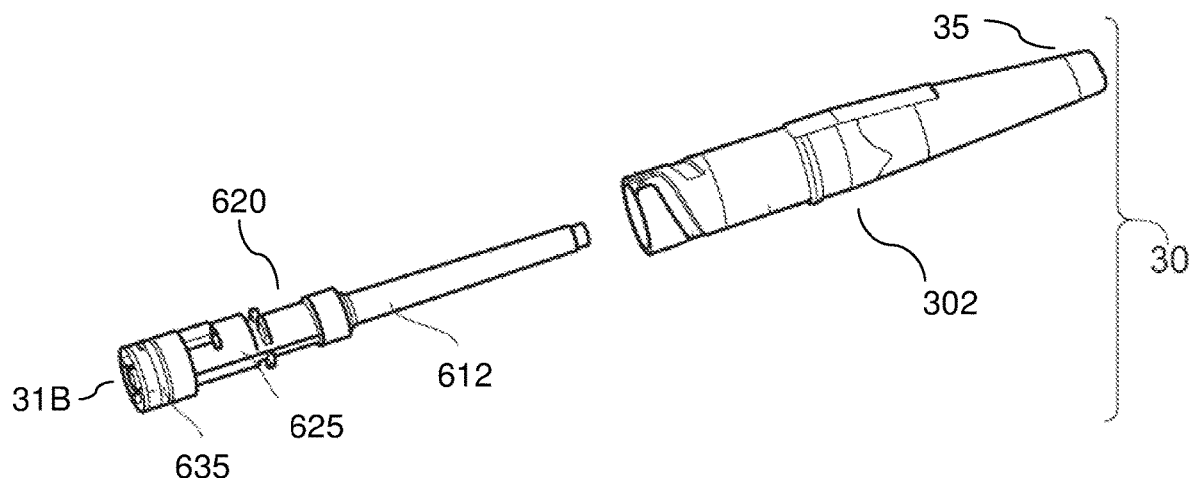
FIG. 5 is a schematic diagram of a cartomizer of an e-cigarette.

FIG. 5 is a schematic, exploded view of an example cartomizer 30 in accordance with some embodiments. The cartomizer has an outer plastic housing 302, a mouthpiece 35 (which may be formed as part of the housing), a vaporizer 620, a hollow inner tube 612, and a connector 31B for attaching to a control unit. An airflow path through the cartomizer 30 starts with an air inlet through connector 31B, then through the interior of vaporizer 625 and hollow tube 612, and finally out through the mouthpiece 35. The cartomizer 30 retains liquid in an annular region between (i) the plastic housing 302, and (ii) the vaporizer 620 and the inner tube 612. The connector 31B is provided with a seal 635 to help maintain liquid in this region and to prevent leakage.

Figure 6:
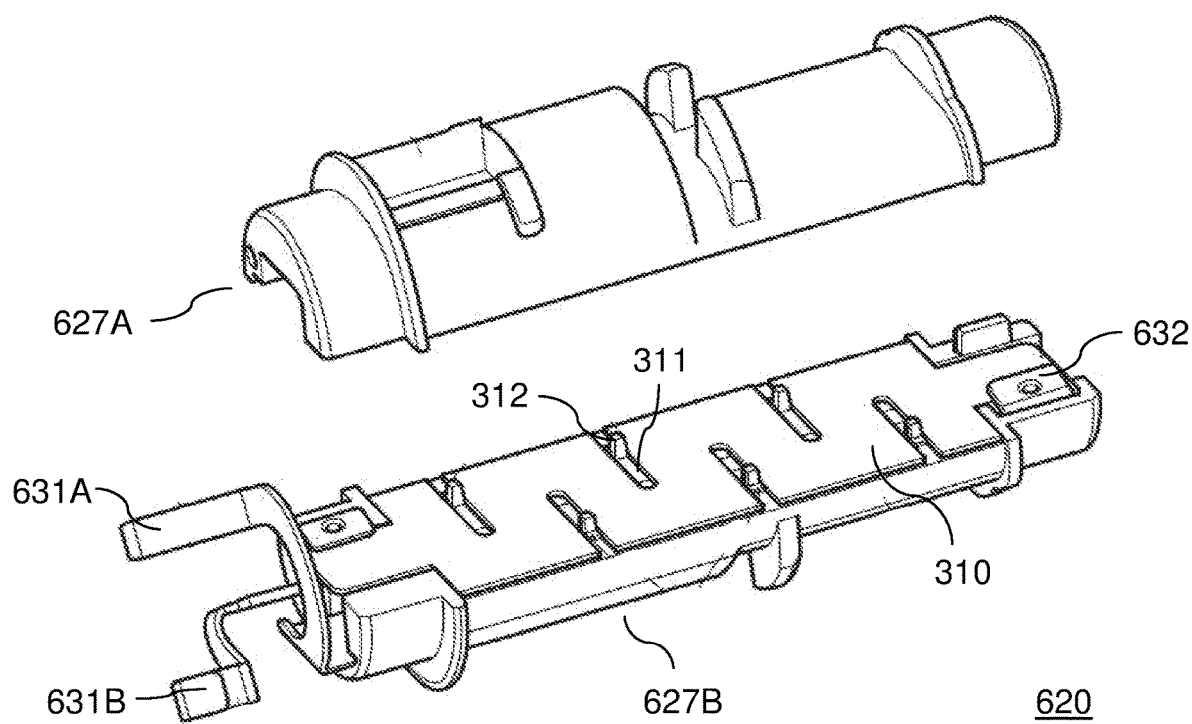
FIG. 6 is a schematic diagram of a vaporizer or heater of an e-cigarette.

FIG. 6 is a schematic, exploded view of the vaporizer 620 from the example cartomizer 30 shown in FIG. 5. The vaporizer 620 has a substantially cylindrical housing (cradle) formed from two components, 627A, 627B, each having a substantially semi-circular cross-section. When assembled, the edges of the components 627A, 627B do not completely abut one another (at least, not along their entire length), but rather a slight gap 625 remains (as indicated in FIG. 5). This gap allows liquid from the outer reservoir around the vaporizer and tube 612 to enter into the interior of the vaporizer 620.

One of the components 627B of the vaporizer is shown in FIG. 6 supporting a heater 310. There are two connectors 631A, 631B shown for supplying power (and a wireless communication signal) to the heater 310. More particular, these connectors 631A, 631B link the heater to connector 31B, and from there to the control unit 20. (Note that connector 631A is joined to pad 632A at the far end of vaporizer 620 from connector 31B by an electrical connection that passes under the heater 310 and which is not visible in FIG. 6).

The heater 310 comprises a heating element formed from a sintered metal fiber material and is generally in the form of a sheet or porous, conducting material (such as steel). However, it will be appreciated that other porous conducting materials may be used. The overall resistance of the heating element in the example of FIG. 6 is around 1 ohm. However, it will be appreciated that other resistances may be selected, for example having regard to the available battery voltage and the desired temperature/power dissipation characteristics of the heating element. In this regard, the relevant characteristics may be selected in accordance with the desired aerosol (vapor) generation properties for the device depending on the source liquid of interest.

The main portion of the heating element is generally rectangular with a length (i.e. in a direction running between the connector 31B and the contact 632A) of around 20 mm and a width of around 8 mm. The thickness of the sheet comprising the heating element in this example is around 0.15 mm.

As can be seen in FIG. 6, the generally-rectangular main portion of the heating element has slots 311 extending inwardly from each of the longer sides. These slots 311 engage pegs 312 provided by vaporizer housing component 627B, thereby helping to maintain the position of the heating element in relation to the housing components 627A, 627B.

The slots extend inwardly by around 4.8 mm and have a width of around 0.6 mm. The slots 311 extending inwardly are separated from one another by around 5.4 mm on each side of the heating element, with the slots extending inwardly from the opposing sides being offset from one another by around half this spacing. A consequence of this arrangement of slots is that current flow along the heating element is in effect forced to follow a meandering path, which results in a concentration of current and electrical power around the ends of the slots. The different current/power densities at different locations on the heating element mean there are areas of relatively high current density that become hotter than areas of relatively low current density.

This in effect provides the heating element with a range of different temperatures and temperature gradients, which can be desirable in the context of aerosol provision systems. This is because different components of a source liquid may aerosolize/vaporize at different temperatures, and so providing a heating element with a range of temperatures can help simultaneously aerosolize a range of different components in the source liquid.

The heater 310 shown in FIG. 6, having a substantially planar shape which is elongated in one direction, is well-suited to act as an antenna. In conjunction with the metal housing 202 of the control unit, the heater 310 forms an approximate dipole configuration, which typically has a physical size of the same order of magnitude as the wavelength of Bluetooth Low Energy communications—i.e. a size of several centimeters (allowing for both the heater 310 and the metal housing 202) against a wavelength of around 12 cm.

Although FIG. 6 illustrates one shape and configuration of the heater 310 (heating element), the skilled person will be aware of various other possibilities. For example, the heater may be provided as a coil or some other configuration of resistive wire. Another possibility is that the heater is configured as a pipe containing liquid to be vaporized (such as some form of tobacco product). In this case, the pipe may be used primarily to transport heat from a place of generation (e.g. by a coil or other heating element) to the liquid to be vaporized. In such a case, the pipe still acts as a heater in respect of the liquid to be heated. Such configurations can again optionally be used as an antenna to support wireless configurations.

As was noted previously herein, a suitable e-cigarette 10 can communicate with a mobile communication device 400, for example by paring the devices using the Bluetooth® low energy protocol.

Consequently, it is possible to provide additional functionality to the e-cigarette and/or to a system comprising the e-cigarette and the smart phone, by providing suitable software instructions (for example in the form of an app) to run on the smart phone.

Figure 7:
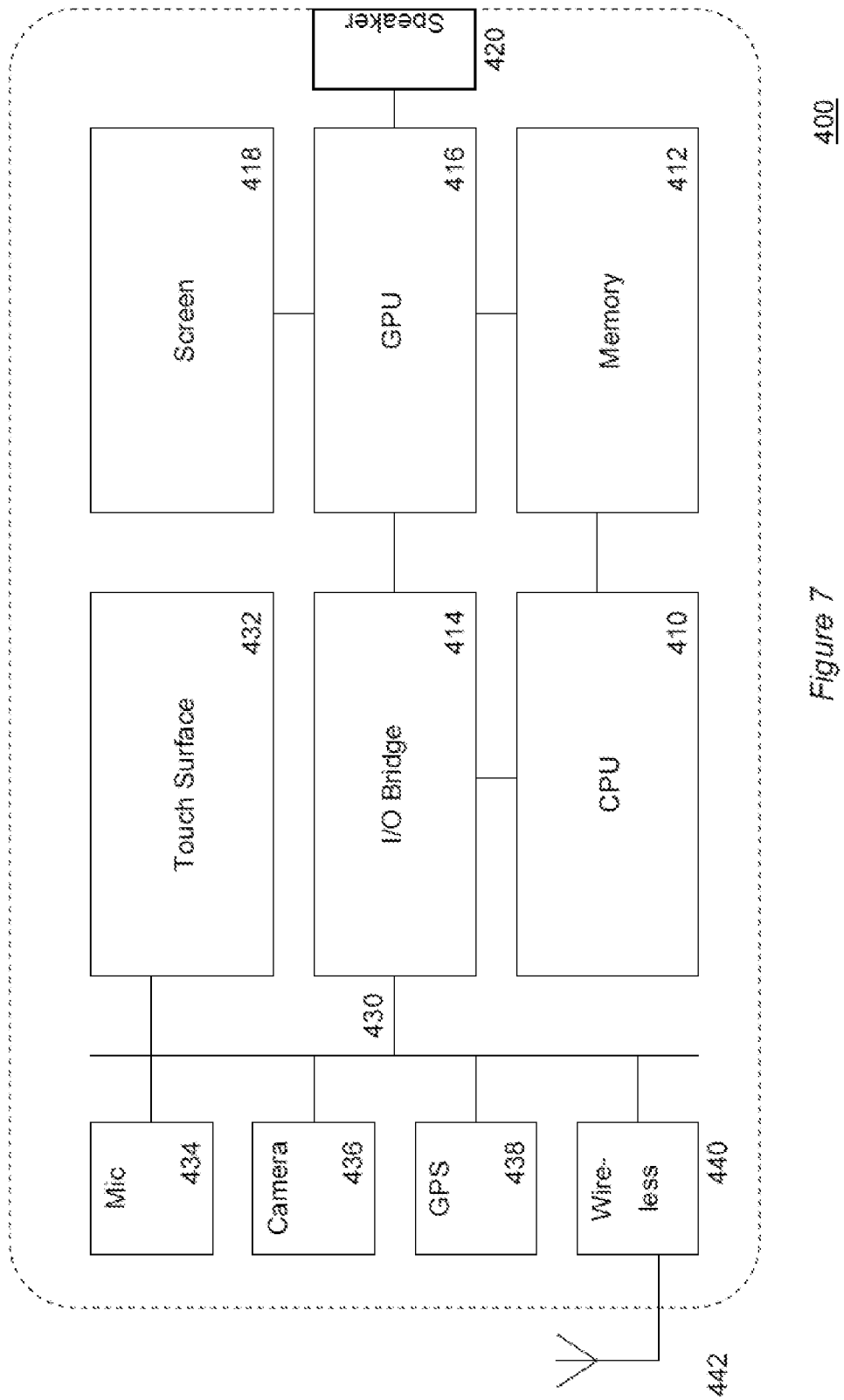
FIG. 7 is a schematic diagram of a mobile terminal in accordance with embodiments of the present disclosure.

Turning now to FIG. 7, a typical smartphone 400 comprises a central processing unit (CPU) (410). The CPU may communicate with components of the smart phone either through direct connections or via an I/O bridge 414 and/or a bus 430 as applicable.

In the example shown in FIG. 7, the CPU communicates directly with a memory 412, which may comprise a persistent memory such as for example Flash® memory for storing an operating system and applications (apps), and volatile memory such as RAM for holding data currently in use by the CPU. Typically persistent and volatile memories are formed by physically distinct units (not shown). In addition, the memory may separately comprise plug-in memory such as a microSD card, and also subscriber information data on a subscriber information module (SIM) (not shown).

The smart phone may also comprise a graphics processing unit (GPU) 416. The GPU may communicate directly with the CPU or via the I/O bridge, or may be part of the CPU. The GPU may share RAM with the CPU or may have its own dedicated RAM (not shown) and is connected to the display 418 of the mobile phone. The display is typically a liquid crystal (LCD) or organic light-emitting diode (OLED) display, but may be any suitable display technology, such as e-ink. Optionally the GPU may also be used to drive one or more loudspeakers 420 of the smart phone.

Alternatively, the speaker may be connected to the CPU via the I/O bridge and the bus. Other components of the smart phone may be similarly connected via the bus, including a touch surface 432 such as a capacitive touch surface overlaid on the screen for the purposes of providing a touch input to the device, a microphone 434 for receiving speech from the user, one or more cameras 436 for capturing images, a global positioning system (GPS) unit 438 for obtaining an estimate of the smart phones geographical position, and wireless communication means 440.

The wireless communication means 440 may in turn comprise several separate wireless communication systems adhering to different standards and/or protocols, such as Bluetooth® (standard or low-energy variants), near field communication and Wi-Fi® as described previously, and also phone based communication such as 2G, 3G and/or 4G.

The systems are typically powered by a battery (not shown) that may be chargeable via a power input (not shown) that in turn may be part of a data link such as USB (not shown).

It will be appreciated that different smartphones may include different features (for example a compass or a buzzer) and may omit some of those listed above (for example a touch surface).

Thus more generally, in an embodiment of the present disclosure a suitable remote device such as smart phone 400 will comprise a CPU and a memory for storing and running an app, and wireless communication means operable to instigate and maintain wireless communication with the e-cigarette 10. It will be appreciated however that the remote device may be a device that has these capabilities, such as a tablet, laptop, smart TV or the like.

One example of additional functionality that may be provided to the e-cigarette 10 and/or to a combination of the e-cigarette 10 and the mobile communication device 400 is the ability to provide results to the user based upon the vapor analysis performed by an electronic breath alcohol testing device attached to the e-cigarette.

With reference to FIG. 1, it will be appreciated that a conventional e-cigarette 10 may be disassembled by a user in to two or three parts; a body or control unit 20 and a cartomizer 30, which in turn may comprise a removable reservoir 38. When assembled, these form a fully and independently operating e-cigarette, with its own power supply, heater, and reservoir.

In embodiments of the present disclosure, an electronic breath alcohol testing device 40 may be detachably coupled to the existing e-cigarette, causing or enabling the breath alcohol testing device to share at least part of an airpath with the e-cigarette, and draw power from it.

Hence the breath alcohol testing device 40, as a separate device, does not need its own power supply, as it uses that of the e-cigarette. Furthermore, it does not need its own mouthpiece, as it uses that of the e-cigarette. Finally, it does not need a wireless communications means, as optionally it uses that of the e-cigarette.

The breath alcohol testing device can tap the airflow path of the e-cigarette at any suitable point. Referring for example to FIG. 1, this may occur for example between the control unit 20 and cartomizer 30, and/or between the cartomizer 30 and mouthpiece 35.

Figure 8:
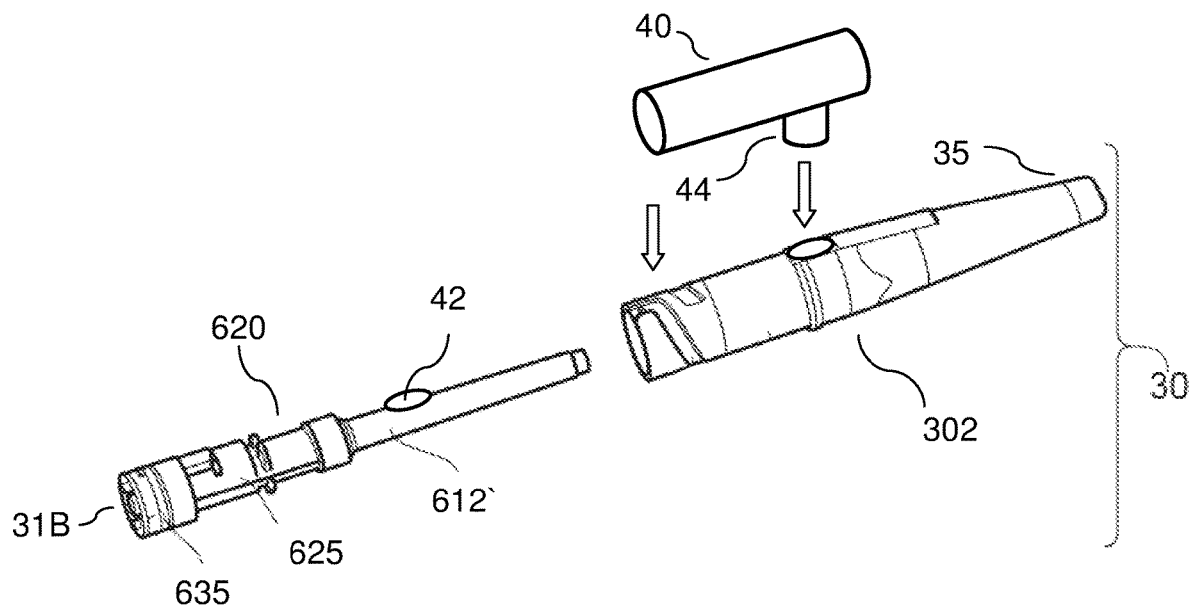
FIG. 8 is a schematic diagram of a cartomizer of an e-cigarette and an electronic breath alcohol testing device in accordance with embodiments of the present disclosure.

With reference now to FIG. 8, the hollow inner tube 612 of FIG. 5 may be adapted to form hollow inner tube 612'. This comprises a valve 42.

Figure 9A:
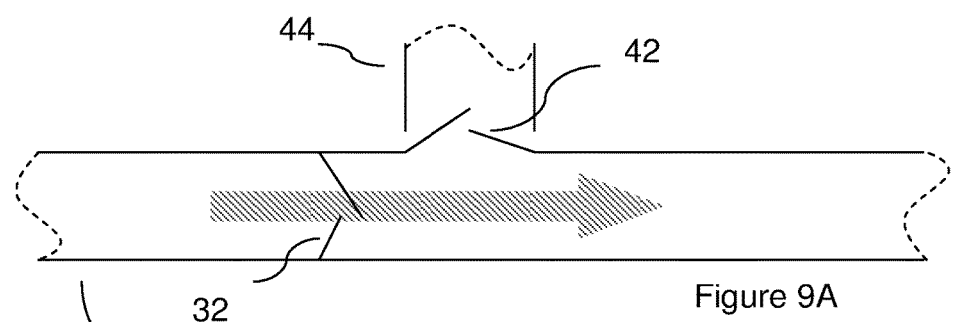
FIGS. 9A and 9B are schematic diagrams of an interaction between an airflow path of an e-cigarette and of an electronic breath alcohol testing device in accordance with embodiments of the present disclosure.
Figure 9B:
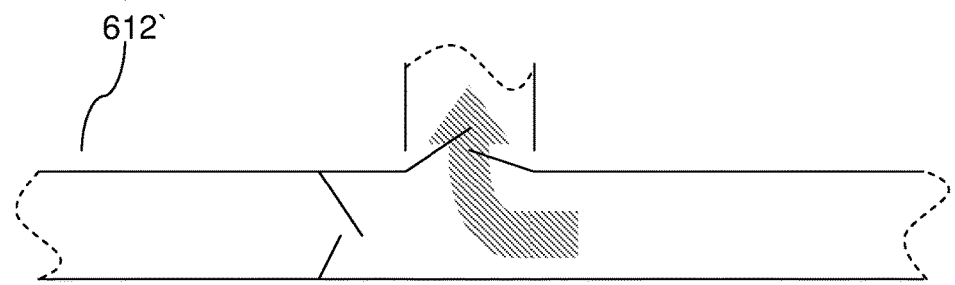

Referring now to FIGS. 9A and 9B, in one embodiment the valve 42 is a one-way valve that allows air to blow out of the tube. The breath alcohol testing device 40 comprises a snorkel (i.e. a tube) 44 operable to pass through a portion of the housing (e.g. via a detachable or slideable hatch) and engage with the valve 42 as a recipient of air blown through the valve.

As shown in FIG. 9A, with the breath alcohol testing device attached to the e-cigarette then when the user inhales, the air flows completely or primarily along the hollow tube 612' towards the user (on the right). However, referring to FIG. 9B, when the user blows back in, a one-way valve in the hollow tube prevents some or all of the airflow beyond a predetermined point in the tube, causing some or all of the air instead to flow up the snorkel and into the breath alcohol testing device. In this manner, potentially both the e-cigarette and the breath alcohol testing device can be operated in succession without further adjustment by the user, depending on whether they inhale on the device (e-cigarette) or exhale into it (breath alcohol testing device).

Figure 10A:
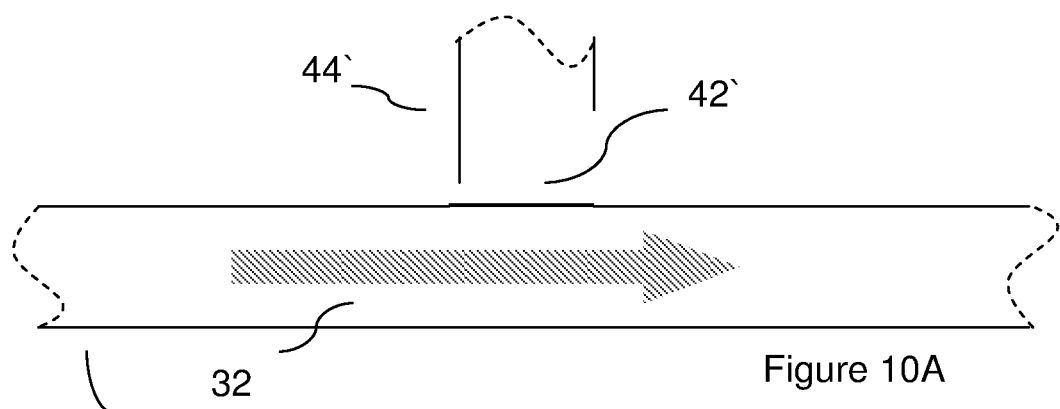
FIGS. 10A and 10B are schematic diagrams of an interaction between an airflow path of an e-cigarette and of an electronic breath alcohol testing device in accordance with embodiments of the present disclosure.
Figure 10B:
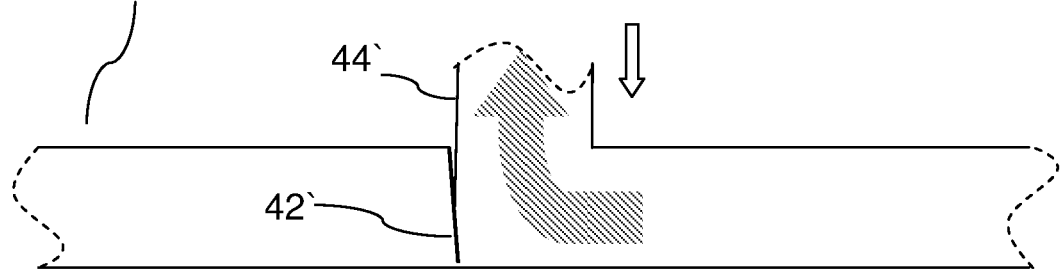

Referring now to FIGS. 10A and 10B, in another embodiment, a valve 42' is opened by a snorkel 44' pushing through it. Hence the breath alcohol testing device 40 comprises a snorkel (i.e. a tube) 44' now operable to pass through a portion of the housing (e.g. via a detachable or slideable hatch) and engage with the valve 42', this time by pushing through it to access the hollow tube 612'.

As shown in FIG. 10A, when the snorkel is not engaged (or only partially engaged—not shown), the user can inhale on the e-cigarette as normal. However, referring to FIG. 10B, when the snorkel is engaged, then if the user blows back in, the air is diverted into the snorkel. The snorkel may be engaged by the action of attaching the breath alcohol testing device to the e-cigarette, such that the e-cigarette effectively changes function for as long as the breath alcohol testing device is attached to it. Alternatively the snorkel may be engaged temporarily, for example by the user pressing down on a portion of the breath alcohol testing device that is mechanically coupled to the snorkel. In this case the user can then press on this portion of the breath alcohol testing device to access the breath alcohol testing device function. The portion may for example be a button that mechanically pushes the snorkel.

It will be appreciated that the above arrangements are non-limiting examples of the breath alcohol testing device sharing at least part of an airflow path with the e-cigarette. In another example shown in FIG. 11, the hollow tube 612 may be differently adapted to form a hollow tube 612" having a resilient portion than can be bent out of line by a snorkel 44" when it is engaged. Again, engagement may occur to the duration of attachment of the breath alcohol testing device to the e-cigarette, or may be caused by an action of the user to move it into the path of the hollow tube.

Hence whilst not shown, it will be appreciated that a button or actuator mechanism for moving the snorkel relative to the airflow path may for example comprise a spring mounted push-button arranged to push the snorkel forward so as to engage with the airflow path so as to access it (as in the case of FIGS. 9A and 9B) or so as to enter into the air flow path (so as to alter or divert the airflow, as in the case of FIGS. 10A, 10B and 11), or similarly a slider arranged to slide the snorkel or the testing device such that an (additional) portion of the snorkel is engaged with or introduced into the air flow path. It will also be appreciated that such a button or actuator mechanism may act to connect power supplied from the e-cigarette to the alcohol sensor and any associated circuitry, so that the device only becomes active when fully engaged with the airflow path of the e-cigarette.

It will be appreciated meanwhile that if the breath alcohol testing device 40 is in-line with the e-cigarette (for example inserted between the cartomizer and the control unit), then the snorkel 44 may simply be that part of the breath alcohol testing device that connects to one or both of the connectors 31B and 21A on the cartomizer 30 and the control unit 20 respectively.

Figure 12:
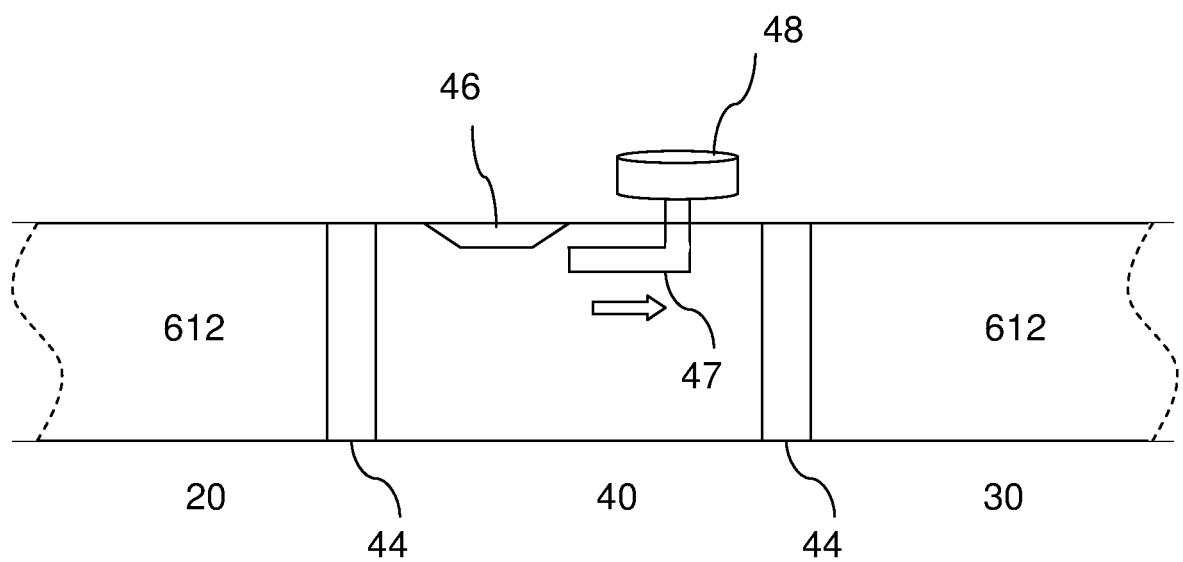
FIG. 12 is a schematic diagram of an interaction between an airflow path of an e-cigarette and of an electronic breath alcohol testing device in accordance with embodiments of the present disclosure.

Hence referring now to FIG. 12, in another example, an in-line breath alcohol testing device unit 40 is placed between the control unit 20 and cartomizer 30 (but may equally sit between the cartomizer and mouthpiece, or at the far end of the e-cigarette from the mouthpiece, if the air flow path through the e-cigarette extends to it). In this case, the snorkel(s) 44 act to connect the breath alcohol testing device to the relevant component(s) of the e-cigarette that share the air-flow path with the breath alcohol testing device. In this case, the user can operate a switch 48 to electrically activate the alcohol sensor 46. Optionally the switch (or a separate mechanism) can be arranged to expose the alcohol sensor to the air flow path shared with the e-cigarette. In FIG. 12, this is achieved by a slider element 47 of the switch moving to expose the sensor to the air flow path (or similarly a levered cover, a shutter/iris or other removable physical cover). Optionally covering the sensor in this way when not in use helps to prevent or limit the build-up of any materials originating from the aerosolized payload/vapor. This may occur to a greater extent in the case of an in-line arrangement, as the breath alcohol testing device may be retained as a supplementary part of the e-cigarette for extended periods.

The breath alcohol testing device itself may use any suitable sensor technology to detect breach alcohol. For example, the Breathalyser® uses a chemical reaction responsive to alcohol that produces a detectable color change. Meanwhile the Intoxilyzer® detects alcohol by infrared (IR) spectroscopy. Alternatively the Alcosensor III or IV® detects a chemical reaction of alcohol in a fuel cell.

In this last case, for example, the Alcosensor works on the principle that in the presence of a catalyst, oxygen in a sample of expired air converts any alcohol present into acetic acid and then to water and carbon dioxide. A fuel cell converts the chemical energy released when oxidation occurs into a detectable electrical voltage. The higher the voltage, the more alcohol is present in the sample.

Hence in each case, the sensor generates a signal responsive to a level of breath alcohol.

This signal may then be conveyed to the control unit of the e-cigarette (for example via electrical contacts made when the breath alcohol testing device is attached to the e-cigarette).

The control unit may then cause the wireless communications interface 55 to transmit the signal (for example via Bluetooth®) to a mobile terminal 400 (e.g. a mobile phone or tablet as shown in FIG. 7) for further processing, for example to calculate a corresponding blood-alcohol level, and display the results.

Alternatively or in addition, the control unit may perform such a calculation itself. Typically the ratio of breath alcohol to blood alcohol 2,100:1. That is to say, 2,100 milliliters (ml) of alveolar air will contain the same amount of alcohol as 1 ml of blood.

Hence based upon the level of alcohol indicated by the sensor it is possible for either a mobile terminal and/or the e-cigarette to calculate an alcohol level. This calculation may be optionally refined if required by further information such as an assumed percentage of the alcohol in an airflow having the proportions of the airflow path within the breath alcohol testing device (e.g. tube diameter) that is detected by the sensor. Similarly the calculation may also optionally use an assumed airflow sample volume, or alternatively measure the amount of airflow, for example based upon a flow detector within the breath alcohol testing device or within the e-cigarette (depending on the placement of the breath alcohol testing device). For example, a change in pressure detected by pressure sensor 62 can be correlated with an airflow speed, and given the diameter of the airflow path; a corresponding volume of air can be calculated. Finally the corresponding amount of alcohol in 1 ml of blood may be calculated as described above.

Optionally, the e-cigarette or the breath alcohol testing device may comprise a user interface for indicating either the blood alcohol concentration, or simply whether this exceeds a legal threshold. Hence for example the e-cigarette or breath alcohol testing device may comprise a red LED lights if the blood alcohol concentration exceeds the legal threshold for the country of the user. It will be appreciated that an application on the mobile terminal 400 could provide a more detailed result such as the calculated but alcohol concentration as well as information relating to whether or not this exceeds the legal threshold. The mobile terminal could also perform further actions responsive to the result, such as offering to call a taxi service if the blood alcohol concentration is above a legal limit.

Figure 11:
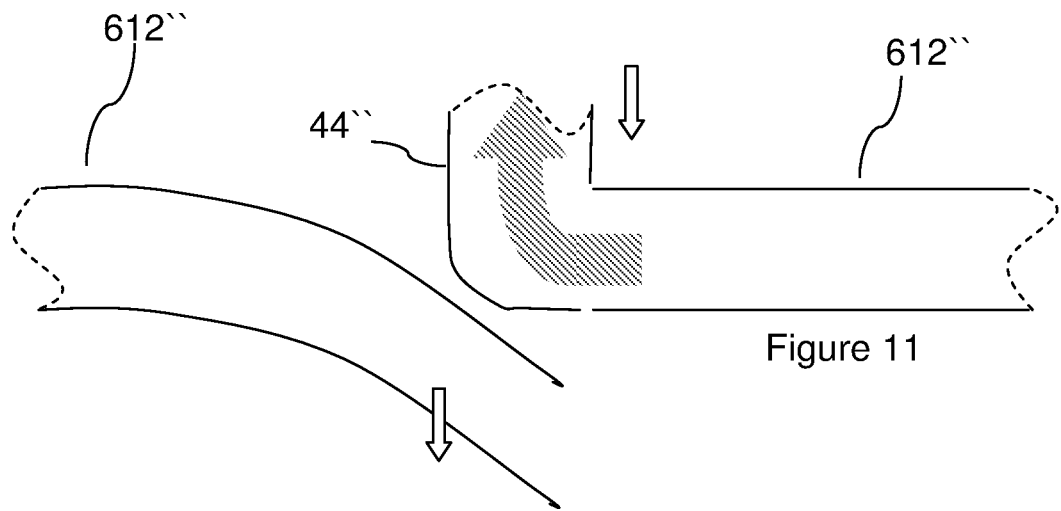
FIG. 11 is a schematic diagram of an interaction between an airflow path of an e-cigarette and of an electronic breath alcohol testing device in accordance with embodiments of the present disclosure.

Hence referring again to FIGS. 8 and 12, in a summary embodiment of the present disclosure, a user monitoring system comprises an e-cigarette 10 comprising a power source 54, and an electronic breath alcohol testing device 40 for detecting alcohol, detachable from the e-cigarette (in other words, attachable and removable), in which when attached, the electronic breath alcohol testing device is operable to share at least part of an airflow path of the e-cigarette (for example as illustrated in FIGS. 8 to 12), and when attached, the electronic breath alcohol testing device is operable to share the power source of the e-cigarette (for example via electrical contacts, not shown, from the power source of the e-cigarette or via a control unit 50 of the e-cigarette).

In an instance of this summary embodiment, the electronic breath alcohol testing device is adapted to access the airflow path (612') of the e-cigarette when physically attached to the e-cigarette, for example via a snorkel 44 as illustrated for example in FIGS. 9A and 9B.

In another instance of this summary embodiment, the electronic breath alcohol testing device is adapted to divert the airflow path (612") of the e-cigarette to the electronic breath alcohol testing device when physically attached to the e-cigarette, as illustrated for example in FIGS. 10A and 10B, and FIG. 11, in the case where attaching the breath alcohol testing device to the e-cigarette causes the snorkel (44', 44") to at least partially alter the existing airflow path.

In another instance of this summary embodiment the electronic breath alcohol testing device comprises an actuation mechanism for moving a snorkel as described previously herein. When attached, the electronic breath alcohol testing device is thus adapted to access the airflow path of the e-cigarette by moving the snorkel to engage with the airflow path upon operation of the actuation mechanism, for example by moving adjacent to a valve 42 in the airflow path as illustrated for example in FIGS. 9A and 9B.

In another instance of this summary embodiment, the electronic breath alcohol testing device comprises an actuation mechanism for moving a snorkel as described previously herein. When attached, the electronic breath alcohol testing device is adapted to divert the airflow path of the e-cigarette to the electronic breath alcohol testing device by moving the snorkel into the airflow path upon operation of the actuation mechanism, as illustrated for example in FIGS. 10A and 10B, and FIG. 11, in the case where operating the actuation mechanism causes the snorkel (44', 44") to at least partially alter the existing airflow path.

In another instance of this summary embodiment, the e-cigarette a blow-back valve 32 adapted to limit airflow into the e-cigarette from the user reaching one or more selected from the list consisting of a payload store of the e-cigarette (e.g. a solid, a gel, or a reservoir of liquid) as moisture and/or alcohol from the user's breath may affect the payload; a heater of the e-cigarette, as again moisture and/or alcohol from the user's breath may adversely interact with the heater; and a control unit of the e-cigarette since again moisture and/or alcohol from the user's breath may adversely interact with the control unit.

In another instance of this summary embodiment, the electronic breath alcohol testing device comprises a movable cover (44, 45) for the alcohol sensor 46. As discussed previously herein this may be of particular use for an in-line implementation of the breath alcohol testing device, as the alcohol sensor may be located within a part of the e-cigarette airflow during normal use of the e-cigarette for protracted periods.

In another instance of this summary embodiment, the e-cigarette comprises a control processor 50, and this receives signals generated by the electronic breath alcohol testing device. The signals (irrespective of their particular format) may be conveyed via electrical contacts between the breath alcohol testing device and the e-cigarette, which in turn are typically conveyed to the control processor via a wired connection, optionally via an analogue to digital converter, which in turn may optionally be part of the control processor.

In this instance, the e-cigarette may comprise a wireless communications unit 55, such as a Bluetooth® low energy communications unit as described previously herein, for communications with a mobile terminal device 400 such as a phone or tablet, and the control processor is adapted to cause the wireless communication circuit to transmit the signals to the mobile terminal device.

Alternatively, in this instance the control processor may process the signals generated by the electronic breath alcohol testing device to detect an alcohol level.

Subsequently, if the e-cigarette comprises a user interface as described previously herein, the control processor of the e-cigarette may control the user interface to provide an indication of the alcohol level to a user of the user monitoring system. Alternatively or in addition, if the e-cigarette comprises the wireless communication unit 55, then the control processor of the e-cigarette may cause the wireless communication circuit to transmit an indication of the alcohol level to the mobile terminal device 400.

Other features of the user monitoring system described herein may also be incorporated into instances of this summary embodiment.

In another summary embodiment of the present disclosure, an e-cigarette 10 is adapted to interact with an electronic breath alcohol testing device 40 to operate as a user monitoring system. The e-cigarette comprises a power source such as the battery 54, an airflow path (612', 612"), adapted to convey air, and vapor generated by the e-cigarette, to the user during an inhalation (with different parts of the airflow path respectively carrying air and vapor suspended within air, depending on the location of the heater within the e-cigarette); and the airflow path is adapted (for example by using a valve 42, 42', or by being flexible) to, in cooperation with the electronic breath alcohol testing device (for example by means of its snorkel interacting with the airflow path), convey breath from the user during an exhalation into the e-cigarette at least along a portion of the airflow path to the electronic breath alcohol testing device when the e-cigarette is interacting with the electronic breath alcohol testing device; and in which the e-cigarette is adapted to provide power to the electronic breath alcohol testing device when the cigarette is interacting with the electronic breath alcohol testing device (for example via electrical contacts, not shown).

In an instance of this summary embodiment, the e-cigarette comprises a control unit 50, which is adapted to receive measurement signals from the electronic breath alcohol testing device much as described previously in the preceding summary embodiment.

In this case, the control unit may then calculate an alcohol level based upon the received signals (either a breath alcohol level, or a blood alcohol level, as described previously herein).

Similarly in this case, the e-cigarette may comprise a wireless communication unit 55, and the control unit is adapted to cause the wireless communication unit to transmit to a remote device (such as a mobile terminal paired using Bluetooth®) one or more selected from the list consisting of the received measurement signals, and the calculated alcohol level.

Other features of the e-cigarette described herein may also be incorporated into instances of this summary embodiment.

In another summary embodiment of the present disclosure, an electronic breath alcohol testing device 40 is adapted to interact with an e-cigarette 10 to operate as a user monitoring system, and the electronic breath alcohol testing device comprises an alcohol sensor 46, a snorkel (44, 44') for interacting with the airflow path (612, 612', 612") of the e-cigarette; and electrical contacts (not shown) to obtain power for operation of the electronic breath alcohol testing device from the e-cigarette.

In an instance of this summary embodiment, the electronic breath alcohol testing device comprises an actuator for moving the snorkel into a position in which it interacts with the airflow path of the e-cigarette (e.g. by engaging with it to allow air flow into it, as per FIGS. 9A and 9B, or by entering into the air flow path, thereby partially or fully blocking it and causing a diversion of airflow into the electronic breath alcohol testing device, as per FIGS. 10A and 10B, or by modifying the existing air flow path to partially replace it, as per FIG. 11).

In another instance of this summary embodiment, the electronic breath alcohol testing device is shaped to match a circumferential profile of the e-cigarette at a location of attachment to the e-cigarette. Where the electronic breath alcohol testing device attaches to a side of the e-cigarette, then this shaping may apply to the portion of the breath alcohol testing device that comes into contact with the e-cigarette. Where the electronic breath alcohol testing device attaches in line with one or more sections of the e-cigarette, then this shaping may apply to the complete circumference of the electronic breath alcohol testing device itself. It will also be appreciated that where the electronic breath alcohol testing device is placed between two existing components of the e-cigarette, such as between the control unit 20 and cartomizer 30, as per FIG. 12, then the electronic breath alcohol testing device may be shaped along its length so that respective ends of the device match the circumvention profile of the respective component of the e-cigarette to which it is joined.

In another instance of this summary embodiment, signals from the alcohol sensor are transmitted to the e-cigarette. Typically this is done via electrical connections (not shown) between the electronic breath alcohol testing device and the e-cigarette.

It will be appreciated that in principle the electronic breath alcohol testing device could instead transmit signals wirelessly to the e-cigarette. However since the electronic breath alcohol testing device already comprises electrical contacts drawing power from the e-cigarette, this is likely to be a more complex approach.

Similarly it will be appreciated that in principle the electronic breath alcohol testing device could transmit signals wirelessly directly to a mobile terminal, without the need to use a wireless communication unit of the e-cigarette. However, it will be appreciated that this is likely to unnecessarily duplicate wireless communication equipment within the user monitoring system, and furthermore in a case where the electronic breath alcohol testing device only receives power when moved into a position where it engages with the airflow path of the e-cigarette, may not successfully pair with the mobile terminal in a timely fashion, thereby requiring the user to maintain the electronic breath alcohol testing device in an electrically engaged position for a longer time than would otherwise be necessary if the signal data was instead passed directly to the e-cigarette itself.

In another summary embodiment of the present disclosure, a mobile terminal 400 comprises a processor 410, a display 418 and a wireless communication unit 440, and the wireless communication unit is adapted to receive a signal from an e-cigarette 10 of a user monitoring system comprising the e-cigarette and an electronic breath alcohol testing device 40 detachably engaged with the e-cigarette, the signal being responsive to an amount of alcohol in a breath sample exhaled by a user into a mouthpiece of the e-cigarette; and the processor is adapted to cause the display to indicate an alcohol level to a user of the mobile terminal, based upon the received signal. The alcohol level may be a breath alcohol level or a blood alcohol level, and the displayed indication may be quantitative (e.g. an alcohol level per milliliter of blood) and/or may be qualitative (e.g. whether or not the alcohol level exceeds a legal limit).

In an instance of this summary embodiment, the mobile terminal comprises a location detecting circuit for detecting a location of the mobile terminal (for example a global positioning system receiver, or the processor being arranged to parse data enabling identification of a location based upon country code, state code, base station identifier or other location-dependent data included within conventional communications between the mobile terminal and one or more base stations), and the processor is adapted to cause the display to indicate whether an alcohol level exceeds a legal limit associated with the location of the mobile terminal (for example by using a look up table linking legal limits for blood-alcohol concentration to respective countries, states etc.).

It will be appreciated that where applicable the above techniques may be carried out on conventional hardware suitably adapted as applicable by software instruction or by the inclusion or substitution of dedicated hardware.

Thus the required adaptation to existing parts of a conventional equivalent device may be implemented in the form of a computer program product comprising processor implementable instructions stored on a non-transitory machine-readable medium such as a floppy disk, optical disk, hard disk, PROM, RAM, flash memory or any combination of these or other storage media, or realized in hardware as an ASIC (application specific integrated circuit) or an FPGA (field programmable gate array) or other configurable circuit suitable to use in adapting the conventional equivalent device. Separately, such a computer program may be transmitted via data signals on a network such as an Ethernet, a wireless network, the Internet, or any combination of these or other networks.

The invention claimed is:

1. A user monitoring system, comprising:
an e-cigarette comprising a power source; and
an electronic breath alcohol testing device for detecting alcohol detachable from the e-cigarette, wherein, when attached to the e-cigarette:
the electronic breath alcohol testing device is operable to share at least part of an airflow path of the e-cigarette, and
the electronic breath alcohol testing device is operable to share the power source of the e-cigarette.

2. The user monitoring system of claim 1, wherein the electronic breath alcohol testing device is adapted to access the airflow path of the e-cigarette when physically attached to the e-cigarette.

3. The user monitoring system of claim 1, wherein the electronic breath alcohol testing device is adapted to divert the airflow path of the e-cigarette to the electronic breath alcohol testing device when physically attached to the e-cigarette.

4. The user monitoring system of claim 1, wherein the electronic breath alcohol testing device comprises an actuation mechanism for moving a snorkel, and when attached to the e-cigarette, the electronic breath alcohol testing device is adapted to access the airflow path of the e-cigarette by moving the snorkel to engage with the airflow path upon operation of the actuation mechanism.

5. The user monitoring system of claim 1, wherein the electronic breath alcohol testing device comprises an actuation mechanism for moving a snorkel, and when attached to the e-cigarette, the electronic breath alcohol testing device is adapted to divert the airflow path of the e-cigarette to the electronic breath alcohol testing device by moving the snorkel into the airflow path upon operation of the actuation mechanism.

6. The user monitoring system of claim 1, wherein the e-cigarette comprises:
a blow-back valve adapted to limit airflow into the e-cigarette from a user reaching one or more selected from the group consisting of:
a payload store of the e-cigarette;
a heater of the e-cigarette; and
a control unit of the e-cigarette.

7. The user monitoring system of claim 1, wherein the electronic breath alcohol testing device comprises a movable cover for an alcohol sensor.

8. The user monitoring system of claim 1, wherein the e-cigarette comprises a control processor, and wherein the control processor receives signals generated by the electronic breath alcohol testing device.

9. The user monitoring system of claim 8, wherein the e-cigarette comprises a wireless communication unit for communications with a mobile terminal device, and wherein the control processor of the e-cigarette is adapted to cause the wireless communication circuit to transmit the signals to the mobile terminal device.

10. The user monitoring system of claim 8, wherein the control processor processes the signals generated by the electronic breath alcohol testing device to detect an alcohol level.

11. The user monitoring system of claim 10, wherein the e-cigarette comprises a user interface, and wherein the control processor of the e-cigarette controls the user interface to provide an indication of the alcohol level to a user of the user monitoring system.

12. The user monitoring system of claim 10, wherein:
the e-cigarette comprises a wireless communication unit for communications with a mobile terminal device, and wherein the control processor of the e-cigarette causes the wireless communication circuit to transmit an indication of the alcohol level to a mobile terminal device.

13. A system, comprising:
a user monitoring system of claim 1; and
a mobile terminal, comprising:
a processor;
a display; and
a wireless communication unit,
wherein:
the wireless communication unit is adapted to receive a signal from an e-cigarette of a user monitoring system comprising the e-cigarette and an electronic breath alcohol testing device detachably engaged with the e-cigarette, the signal being responsive to an amount of alcohol in a breath sample exhaled by a user into a mouthpiece of the e-cigarette; and
the processor is adapted to cause the display to indicate an alcohol level to a user of the mobile terminal, based upon the received signal.

14. The system of claim 13, wherein the mobile terminal comprises a location detecting circuit for detecting a location of the mobile terminal, wherein the processor is adapted to cause the display to indicate whether an alcohol level exceeds a legal limit associated with the location of the mobile terminal.

15. An e-cigarette adapted to interact with an electronic breath alcohol testing device to operate as a user monitoring system, the e-cigarette comprising:
a power source; and
an airflow path adapted to convey air and vapor generated by the e-cigarette to the user during an inhalation, and adapted to, in cooperation with electronic breath alcohol testing device, convey breath from the user during an exhalation into the e-cigarette at least along a portion of the airflow path to the electronic breath alcohol testing device when the e-cigarette is interacting with the electronic breath alcohol testing device;
and wherein the e-cigarette is adapted to provide power to the electronic breath alcohol testing device when the e-cigarette is interacting with the electronic breath alcohol testing device.

16. The e-cigarette of claim 15, further comprising:
a control unit adapted to receive measurement signals from the electronic breath alcohol testing device and to calculate an alcohol level based upon the received measurement signals.

17. The e-cigarette of claim 16, further comprising:
a wireless communication unit, wherein:
the control unit is adapted to cause the wireless communication unit to transmit to a remote device one or more selected from the group consisting of:
the received measurement signals; and
the calculated alcohol level.

18. An electronic breath alcohol testing device adapted to interact with an e-cigarette to operate as a user monitoring system, the electronic breath alcohol testing device comprising:
an alcohol sensor;

a snorkel for interacting with an airflow path of the e-cigarette; and electrical contacts to obtain power for operation of the electronic breath alcohol testing device from the e-cigarette.

19. The electronic breath alcohol testing device of claim 18, further comprising an actuator for moving the snorkel into a position in which the snorkel interacts with the airflow path of the e-cigarette.

20. The electronic breath alcohol testing device of claim 18, wherein signals from the alcohol sensor are transmitted to the e-cigarette.

* * * * *